(12) United States Patent
Tamura et al.

(10) Patent No.: US 9,841,389 B2
(45) Date of Patent: Dec. 12, 2017

(54) PHOTON-COUNTING TYPE X-RAY COMPUTED TOMOGRAPHY APPARATUS AND METHOD

(71) Applicant: TOSHIBA MEDICAL SYSTEMS CORPORATION, Otawara-Shi (JP)

(72) Inventors: Emi Tamura, Nasushiobara (JP); Yasuo Saito, Nasushiobara (JP); Takuzo Takayama, Utsunomiya (JP); Hiroaki Miyazaki, Otawara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 147 days.

(21) Appl. No.: 14/596,457

(22) Filed: Jan. 14, 2015

(65) Prior Publication Data

US 2015/0198725 A1   Jul. 16, 2015

(30) Foreign Application Priority Data

Jan. 14, 2014   (JP) ................. P2014-004538

(51) Int. Cl.

| | | |
|---|---|---|
| *G01T 1/24* | (2006.01) | |
| *G01N 23/04* | (2006.01) | |
| *G01T 1/17* | (2006.01) | |
| *G01T 1/29* | (2006.01) | |
| *A61B 6/03* | (2006.01) | |
| *A61B 6/00* | (2006.01) | |

(52) U.S. Cl.
CPC .......... *G01N 23/046* (2013.01); *A61B 6/032* (2013.01); *A61B 6/4241* (2013.01); *A61B 6/482* (2013.01); *G01T 1/17* (2013.01); *G01T 1/2985* (2013.01)

(58) Field of Classification Search
CPC .. G01T 1/17; G01T 1/18; G01T 1/247; G01T 1/482; G01T 1/502; G01T 1/2018; G01T 1/2985; A61B 6/032; A61B 6/035; A61B 6/4241; A61B 6/482; G01N 23/046
See application file for complete search history.

(56) References Cited

U.S. PATENT DOCUMENTS

2014/0105370 A1*  4/2014  Yamakawa ............ A61B 6/025
                                                         378/207
2014/0328466 A1* 11/2014  Proksa .................... G06F 7/64
                                                         378/62

FOREIGN PATENT DOCUMENTS

JP      P2012-034901       2/2012

* cited by examiner

*Primary Examiner* — David E Smith
*Assistant Examiner* — Hsien Tsai
(74) *Attorney, Agent, or Firm* — Oblon, McClelland, Maier & Neustadt, L.L.P.

(57) ABSTRACT

A photon-counting type X-ray computed tomography apparatus that comprises a high-voltage generator to generate a voltage signal, an X-ray tube to emit X-rays when the X-ray tube receives the voltage signal from the high-voltage generator, an X-ray detector to detect photons derived from the X-rays emitted from the X-ray tube, and circuitry to count a number of the detected photons with respect to a plurality of energy bands, detect a number of photons in a first energy band that exceeds an energy level corresponding to a voltage value of the voltage signal, and changing a number of photons at a second energy band based on the detected number of photons in the first energy band, to correct for operational limitations of the X-ray detector.

12 Claims, 11 Drawing Sheets

(a) X-ray path (b) X-ray spectrum

Count-material table

| ID | Count (input) | Material Length (output) |
|---|---|---|
| 1 | $\begin{pmatrix} C_{11} \\ C_{21} \end{pmatrix}$ | $\begin{pmatrix} L_{s1} \\ L_{h1} \end{pmatrix}$ |
| 2 | $\begin{pmatrix} C_{12} \\ C_{22} \end{pmatrix}$ | $\begin{pmatrix} L_{s2} \\ L_{h2} \end{pmatrix}$ |
| 3 | $\begin{pmatrix} C_{13} \\ C_{23} \end{pmatrix}$ | $\begin{pmatrix} L_{s3} \\ L_{h3} \end{pmatrix}$ |
| ⋮ | ⋮ | ⋮ |

Fig. 9

Material-response table

| ID | Material length (input) | Response function (output) |
|---|---|---|
| 1 | $\begin{pmatrix} L_{s1} \\ L_{h1} \end{pmatrix}$ | Resp1 |
| 2 | $\begin{pmatrix} L_{s2} \\ L_{h2} \end{pmatrix}$ | Resp2 |
| 3 | $\begin{pmatrix} L_{s3} \\ L_{h3} \end{pmatrix}$ | Resp3 |
| ⋮ | ⋮ | ⋮ |

PHOTON-COUNTING TYPE X-RAY COMPUTED TOMOGRAPHY APPARATUS AND METHOD

CROSS-REFERENCE TO RELATED APPLICATIONS

This application is based upon and claims the benefit of priority from prior Japanese Patent Application No. 2014-4538, filed Jan. 14, 2014, the entire contents of which are incorporated herein by reference.

FIELD

Embodiments herein relate to a photon-counting type X-ray computed tomography apparatus and method.

DESCRIPTION OF THE RELATED ART

A photon-counting type X-ray computed tomography apparatus (a photon-counting CT) emits X-ray photons toward a target subject. The photon-counting CT counts the number of X-ray photons with respect to each energy band (energy bin) of the X-ray photons. Then, the photon-counting CT generates a photon-counting CT image by using the number of X-ray photons counted in the target energy bin. When the photon-counting CT counts the number of X-ray photons, a pile-up phenomenon can distort the count of the X-ray photons.

The photon-counting CT uses X-ray detectors to detect and count the number of X-ray photons. Each of X-ray detectors has a slightly different characteristic of its detection performance. This difference and the pile-up phenomenon distorts the measured energy spectrum from the actual energy spectrum. This difference between the measured energy spectrum and the actual energy spectrum causes a degraded output photon-counting CT image.

SUMMARY

The present embodiments have been made in consideration of the above situation, and provide a good quality image by correcting the difference between the measured energy spectrum and the actual energy spectrum.

In one embodiment, a photon-counting type X-ray computed tomography apparatus comprises a high-voltage generator configured to generate a voltage signal, an X-ray tube configured to emit X-rays when the X-ray tube receives the voltage signal from the high-voltage generator, an X-ray detector configured to detect photons derived from the X-rays emitted from the X-ray tube, and circuitry configured to count a number of the detected photons with respect to a plurality of energy bands, detect a number of the photons at a first energy band that exceeds an energy level corresponding to a voltage value of the voltage signal, and changing a number of the photons at a second energy band, based on the detected number of photons at the first energy band, to correct for operational limitations of the X-ray detector.

DETAILED DESCRIPTION

Embodiments of the present disclosure will be described below with reference to the views of the accompanying drawings. Note that the same reference numerals denote constituent elements having substantially the same functions and arrangements, and a repetitive description will be made only when required.

Figure 1:
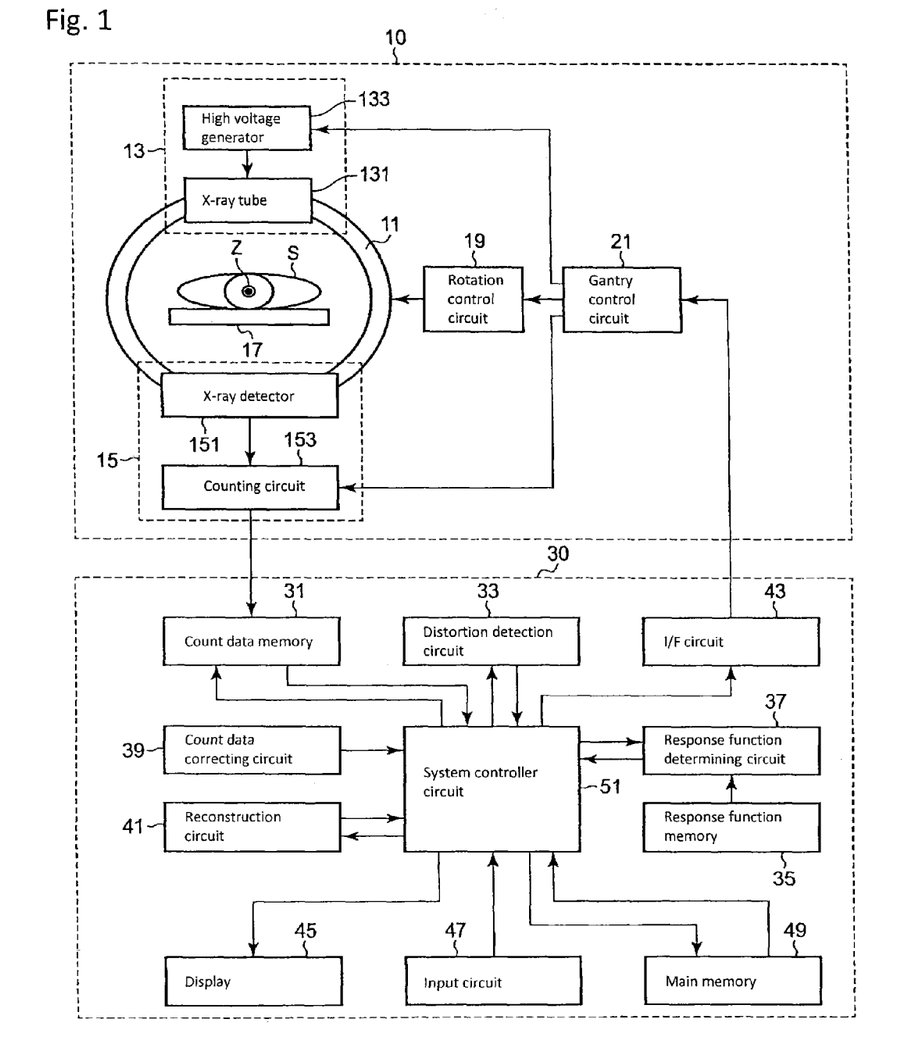
FIG. 1 is a block diagram of a photon-counting CT according to an embodiment.

FIG. 1 is a block diagram of a photon-counting type X-ray computed tomography apparatus (a photon-counting CT scanner) according to one embodiment. As shown in FIG. 1, the photon-counting CT has a gantry 10 and a console 30. The gantry 10 has a rotating frame 11 that has a tube shape and rotates about a rotational axis Z. The rotating frame 11 has an X-ray generator circuit 13 and an X-ray detection circuit 15. The X-ray generator circuit 13 and the X-ray detection circuit 15 face each other across the rotational axis Z. The rotating frame 11 has a bore and a subject table 17 moves inside of the bore when the subject is scanned, in order to place a target area inside of a field of view (FOV). A subject S is placed on the subject table 17. The rotating frame 11 has a motor that rotates the rotating frame 11 about the rotate axis Z with a specific speed. A rotation control circuit 19 is an electronic circuit that generates electric signals to the motor inside of the rotating frame 11 for rotating the rotating frame 11, based on control signals from a gantry control circuit 21.

The X-ray generator circuit 13 is electric circuitry that has an X-ray tube 131 and a high-voltage generator 133. The X-ray generator circuit 13 drives the X-ray tube 131 and the high-voltage generator 133 in order to generate X-rays from the X-ray tube 131, based on the control signals from the gantry control circuit 21. When the X-ray tube 131 receives high-voltage signals and filament currents from the high voltage generator 133, the X-ray tube 131 emits the X-rays. The high-voltage generator 133 inputs the high-voltage signals and the filament currents to the X-ray tube 131 when X-ray generator circuit 13 inputs control signals to the high-voltage generator 133.

The X-ray detection circuit 15 is electric circuitry and includes the X-ray detectors 151 and the counting circuit 153. The X-ray detection circuit 15 outputs count data that shows the number of the detected X-ray photons in each of the energy bins.

The X-ray detector 151 detects the X-ray photons that are generated by the X-ray tube 131 and go through the subject S. The X-ray detector 151 is a 2-D array of X-ray detection cells. Each X-ray detection cell is a semiconductor detector and generates electrical pulses (electric signals) when the X-ray photon enters the X-ray detection cell. The height of each electrical pulse varies by energy level of the incoming X-ray photon. Concretely, the X-ray detection cell is a semiconductor diode that has electric contacts at both sides. The incoming X-ray photon is converted into an electron-hole pair. The number of electron-hole pairs generated by one incoming incident X-ray depends on the energy level of the incoming X-ray photon. The electron and the hole move the electric contacts on both sides, and this movement results in the electrical pulse. The height of the electrical pulse depends on the number of the electron-hole pairs. In order to convert the X-ray photon into the electron-hole pair efficiently, in one embodiment, the semiconductor diode is made from a material that has a high atomic number, like CdTe and CdZnTe. Note that the X-ray detector can be an indirect type of X-ray detector, instead of the semiconductor detector shown above. The indirect type of X-ray detector has a scintillator that converts the X-ray photon into a photon, and a photosensor that converts the photon into an electric pulse.

The counting circuit 153 is comprised of electronic circuitry. A component of the counting circuit 153 is described later by using FIG. 6. The counting circuit 153 gathers the count data with respect to a plurality of energy bins. The count data represents a number of the counted X-ray photons. The counting circuit 153 is configured to gather the count data in two ways: a sinogram mode method and a list-mode method.

In the sinogram mode method, the counting circuit 153 detects the energy level of the X-ray photon by using the height of an electric pulse. Then the counting circuit 153 counts the number of the X-ray photons by counting the number of the electric pulses with respect to each of the energy bins. The counting circuit 153 gathers the count data, representing the number of X-ray photons with respect to the each of the energy bins, the views, and the X-ray detector cells.

In the list-mode method, the counting circuit 153 detects the energy level of the X-ray photon and the timing when the X-ray photon enters into the X-ray detector 151. The counting circuit 153 generates the count data in a certain time window by referencing the timing when the X-ray photon comes into the X-ray detector 151. Similar to the sinogram mode, the counting circuit 153 generates the count data with respect to each of the energy bins, the views, and the X-ray detector cells.

When the count data is generated by the counting circuit 153, the counting circuit 153 groups a plurality of the energy bins into a target bin or a correction bin. The target bin is used for generating images as described below, and the correction bin is used for correcting distortion caused by the pile-up phenomena and the characteristics of the X-ray detector 151. For making this explanation simpler, the number of the counted X-ray photons with respect to each of the energy bins, the views, and the X-ray detector cells is referred to as the "count data."

The gantry control circuit 21 is a electronic circuit that controls connected components in the gantry 10 by inputting the control signals. For example, for executing a CT scan, the gantry control circuit 21 causes the X-ray generator circuit 13 to emit X-rays, causes the X-ray detection circuit 15 to detect the transmitted X-rays, and causes the rotating control circuit 19 to rotate the X-ray generator circuit 13 and the X-ray detection circuit 15 about the rotational axis Z. The rotation of the rotating control circuit 19 is controlled by the control signals from the gantry control circuit 21. The X-ray generator circuit 13 emits the X-rays when the high-voltage generator 133 inputs the high-voltage signals and the filament currents to the X-ray tube 131, when the X-ray generator circuit 11 receives the control signals from the gantry control circuit 21. The counting circuit 153 of the X-ray detection circuit 15 gathers the count data in a synchronized manner to a timing of the X-ray emission.

The console 30 is comprised of circuitry that includes a plurality of circuits: a count data memory 31, a response function memory 35, a response function determining circuit 37, a count data correcting circuit 39, a reconstruction circuit 41, a distortion detection circuit 33, an I/F circuit 43, a display 45, an input circuit 47, a main memory 49, and a system controller circuit 51.

The count data memory 31 is a data storage like a RAM, a ROM, and/or a hard disk drive. The count data memory 31 stores the count data output from the X-ray detection circuit 15 via the I/F circuit 43. The count data is stored with respect to each of the energy bins, the views, and the X-ray detector cells. The count data memory 31 can store the corrected count data corrected by the count data correcting unit 39.

The distortion detection circuit 33 is comprised of processing circuitry like a CPU, a FPGA, and/or a microprocessor. The distortion detection circuit 33 checks whether the count data in the target bin has distortion or not by referencing the count data in the correction bin. The distortion detection circuit 33 checks for this distortion for each of the views and the X-ray paths.

The response function memory 35 is a data storage like a RAM, a ROM, and/or a hard disk drive. The response function memory 35 stores response functions that convert the measured energy spectrum into the actual energy spectrum. The response function memory 35 stores the response functions as a look-up-table that associates the count data in the correction bin and the response function. That is, when the count data in the correction bin is determined (measured), the response function can be determined by referencing the look-up-table data in the response function memory 35. This look-up-table data is called a count-response table in this embodiment. This count-response table is read out by the response function determining circuit 37.

The response function determining circuit 37 is comprised of processing circuitry like a CPU, a FPGA, and/or a microprocessor, which is configured to execute program instructions to implement the functions described below and shown in FIG. 10. In particular, the response function determining circuit 37 determines the response function by using the count-response table in the response function memory 35 and the count data in the correction bin. The correction bin has an energy band that exceeds the value of the high-voltage signal that is inputted into the X-ray tube 131. The response function represents an amount of the distortion between the measured energy spectrum and the actual energy spectrum. Specifically, when the response function determining circuit 37 detects the distortion for a specific X-ray path, the response function determining circuit 37 determines the response function for the specific X-ray path. The response function determining circuit 37 determines the response function for the X-ray path by using the count-response table and the count data for the specific X-ray path. Note that when a relationship between the count data in the correction bin and the response functions is defined by a specific formula or a specific algorithm, the response function determining circuit 37 can determine the response function for the X-ray path by using this specific formula or algorithm, instead of using the count-response table.

The count data correcting circuit 39 is comprised of processing circuitry like a CPU, a FPGA, and/or a microprocessor. The count data correcting circuit 39 changes (corrects) the count data by applying the determined response function to the count data in the target bin. Specifically, when the response function determining circuit 37 detects the distortion for the specific X-ray path, the count data correcting circuit 39 applies the determined response function to the count data in the target bin and for the specific X-ray path. The count data that has been applied to the response function is called the collected count data in this embodiment.

The reconstruction circuit 41 is comprised of processing circuitry like a CPU, a FPGA, and/or a microprocessor. The reconstruction circuit 41 generates photon-counting CT images by applying a well-known reconstruction algorithm to the count data. The reconstruction circuit 41 can reconstruct the photon-counting CT images from the count data, the corrected count data, and a mixture of the count data and the corrected count data.

The I/F circuit 43 is an electronic circuit that exchanges electric signals between the console 30 and the gantry 10. For example, the I/F circuit 43 receives a control signal that commands starting the CT scan and stopping the CT scan, and sends them to the gantry control circuit 21.

The display 45 is a display like a CRT display, a liquid-crystal display, an electroluminescence display, and a plasma display. The display 45 displays the photon-counting CT images and a result of the detection by the distortion detection circuit 33.

The input circuit 23 is an interface circuit like push buttons, a keyboard, a mouse device, and a switch. The input circuit 23 inputs an input signal into the system controller circuit 51 by a responding operation to the interface circuit.

The main memory 49 is a data storage like a RAM, a ROM, and/or a hard disk drive. The main memory 49 stores algorithms for reconstructing the photon-counting CT images.

The system controller circuit 51 is comprised of processing circuitry like a CPU, a FPGA, and/or a microprocessor. The system controller circuit 51 controls the connected components shown in FIG. 1. The system controller circuit 51 controls the components by inputting control signals for executing the CT scan and generating the photon-counting CT images.

Figure 2:
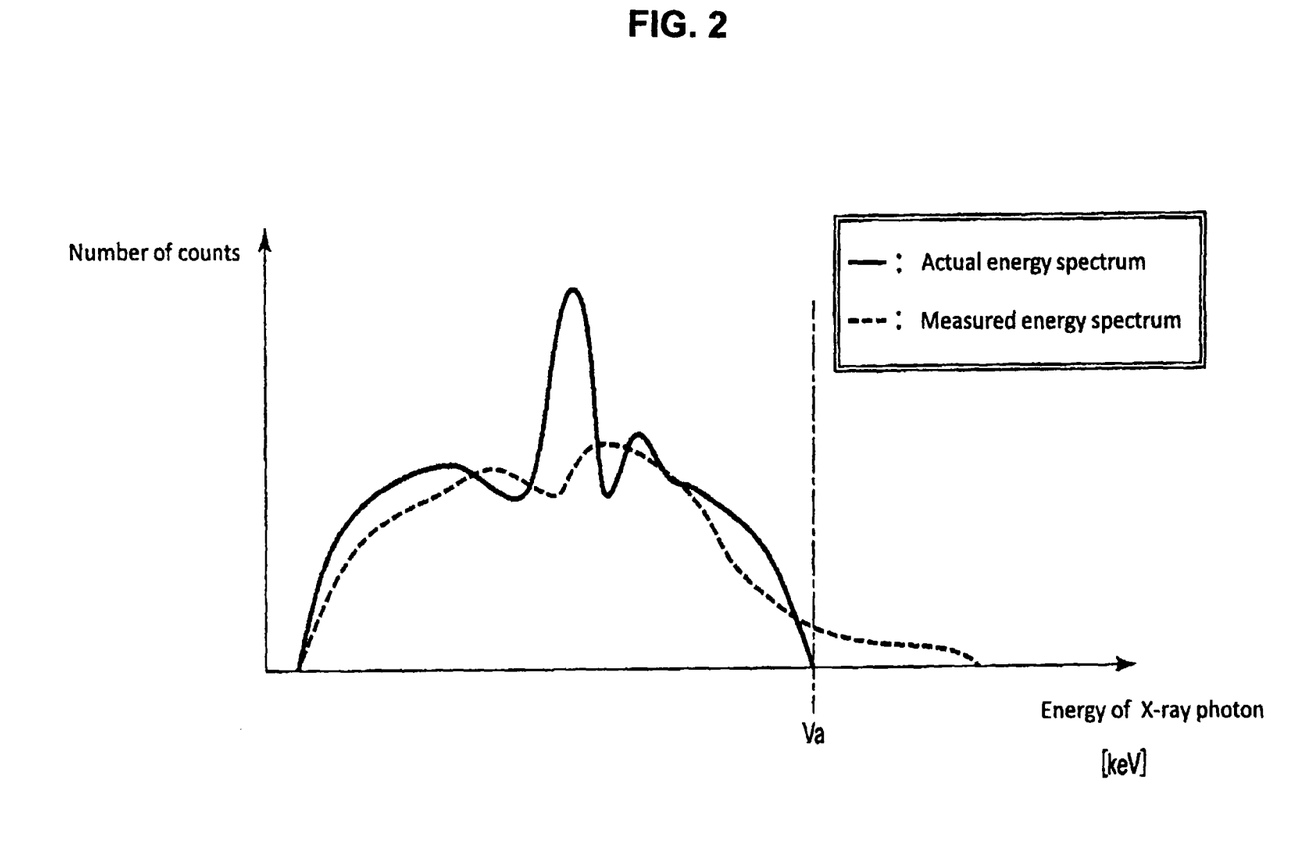
FIG. 2 shows diagrams of a measured energy spectrum and an actual energy spectrum.

The distortion between the measured energy spectrum and the actual energy spectrum will now be described. FIG. 2 shows a measured energy spectrum and an actual energy spectrum. The vertical axis of FIG. 2 shows the number of counts and the horizontal axis shows energy of the X-ray photon (in units of [keV]). The solid line in FIG. 2 shows the actual energy spectrum and the dashed line shows the measured energy spectrum. The actual energy spectrum represents a spectrum of the X-rays emitted from the X-ray tube 131, when the X-ray tube 131 receives a certain high-voltage signal from the high-voltage generator 133. The measured energy spectrum represents the number of counts with respect to each of the energy levels detected by the X-ray detection circuit 15. Note that the measured energy spectrum in FIG. 2 is detected when a specific subject that absorbs the X-ray is not located between the X-ray generator circuit 13 and the X-ray detection circuit 15.

As FIG. 2 shows, when an amount of the high-voltage signal is set at Va [V], the maximum energy of the actual energy spectrum is Va [keV]. That is, the actual energy spectrum is distributed below Va [keV]. The pile-up phenomena occurs when two or more X-ray photons enter one X-ray detector 151 at approximately the same time. In this case, the X-ray detector 151 counts the two or more X-ray photons as one count. Then, the X-ray detector 151 generates an electric pulse with a higher energy value than the original energy value of a single X-ray photon. As a result, the counting circuit 153 generates count data that causes the measured energy spectrum to contain counts at a higher energy level than the actual energy spectrum. As shown in FIG. 2, the measured energy spectrum contains some counts exceeding the energy level of Va [keV]. As described above, the pile-up phenomena distorts the measured energy spectrum from the actual measured energy spectrum.

FIGS. 3(a) and 3(b) show a dependency between the incoming energy spectrum and the X-ray path. FIG. 3(a) shows the X-ray paths, and FIG. 3(b) shows the actual energy spectrum with respect to each of the X-ray paths indicated in FIG. 3(a). As shown in FIG. 3(a), the X-rays emitted from the X-ray tube 131 goes to the X-ray detector 151 through the subject S. FIG. 3(a) shows two types of X-ray paths, P1 and P2. At the X-ray detector 151, the X-ray on the path P2 that goes through an edge of the subject S has more energy than the path P1 that goes through a center of the subject S because the path P2 contains fewer tissues that absorb the X-rays. Then, as shown in FIG. 3(b), the number of photon counts for the path P2 is bigger than for the path P1. The event probability of the pile-up phenomena is increased when X-rays with a high energy enter into the X-ray detector. That is, the path P2 has a higher probability of the pile-up phenomena than the path P1.

As described above, when the pile-up phenomena occurs, the measured energy spectrum is shifted to include a higher energy level than in the actual energy spectrum, and the measured energy spectrum exceeds the maximum energy level Va [keV]. In other words, the distortion detection circuit 33 can detect this distortion by checking the count data that exceeds the maximum energy level. In this embodiment, the distortion detection circuit 33 detects this distortion when the X-rays with high energy enter into the X-ray detector 151.

Figure 4:
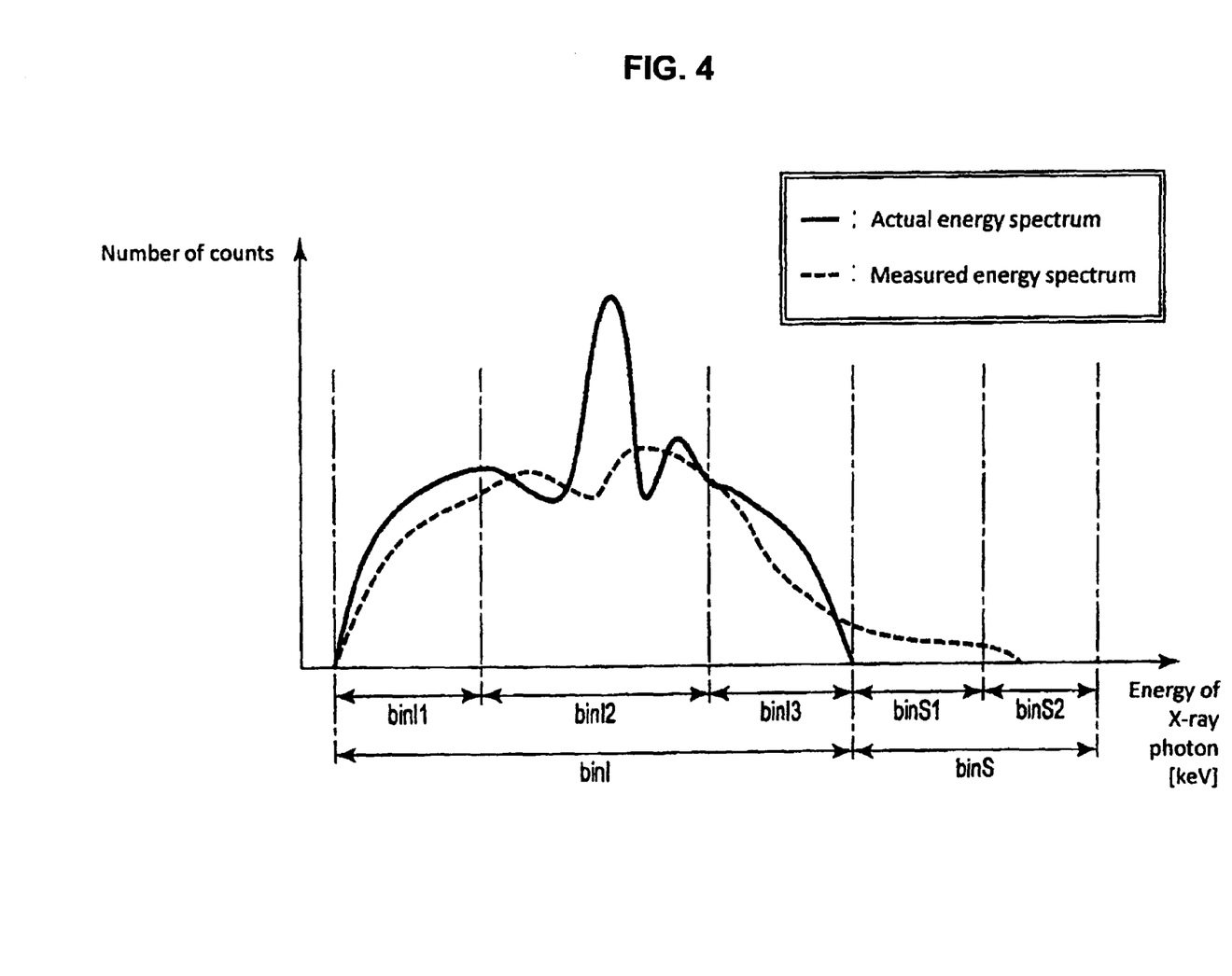
FIG. 4 shows an example of a measured energy spectrum and an actual energy spectrum.

FIG. 4 shows the energy bins set to the measured energy spectrum by the counting circuit 153. In this embodiment, each energy bin represents an energy window of the X-rays. As shown in FIG. 4, the target bins "bin I" that are used for generating images are set below the maximum energy level Va [keV]. For example, in FIG. 4, the counting circuit 153 sets the 3 target bins "bin I1", "bin I2", and "bin I3". In this embodiment, the counting circuit 153 sets the correction bins "bin S" that are used for detecting the distortion above the maximum energy level Va [keV]. For example, in FIG. 4, the counting circuit 153 sets 2 correction bins "bin S1" and "bin S2". When X-rays with high energy enter into the X-ray detector 153, N ("N" represents an integer above 1) X-ray photons can enter into the one X-ray detector 153 at about the same time, which is the pile-up phenomena. The X-ray detector 153 generates an electric signal with a height N times higher than the single X-ray photon. For example, when two X-ray photons enter into the X-ray detector 153 at about the same time, the X-ray detector 153 generates an electric signal with a height about two times higher than that for a single X-ray photon. The correction bins can be distributed in a range from Va [keV] to 2*Va [keV] because there is a low possibility that three or more X-ray photons enter into one X-ray detector 153 at about the same time, when the X-ray is emitted for the purpose of scanning a human body.

A detection characteristic of the X-ray detector 153 also can cause a distortion to the measured energy spectrum. When one of the X-ray detectors 153 is too sensitive for detecting X-ray photons, the measured energy spectrum may exceed the maximum energy Va [keV] and can be detected as a distortion.

Figure 5:
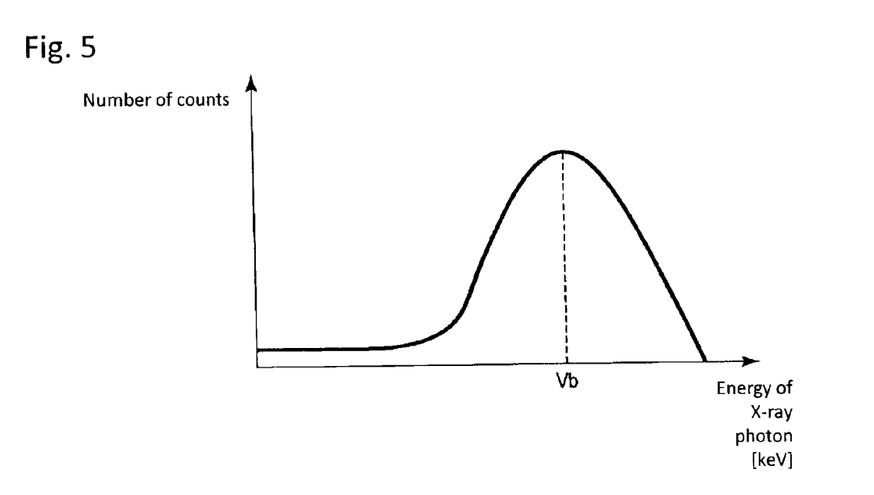
FIG. 5 shows a response function of X-ray detectors regarding to a monochromatic X-ray that has a center energy of Vb [keV].

FIG. 5 shows an example of a response function that represents an ideal output spectrum from the X-ray detection circuit 15 when a monochromatic X-ray photon with an energy of Vb [keV] enters into the X-ray detector 151. A vertical axis in FIG. 5 represents the number of counts, and the horizontal axis represents the energy of detected X-ray photons [keV]. In general, the response function of the X-ray detection circuit 15 has the center energy Vb [keV], is distributed as a Gaussian distribution, and has a tail at a side of the lower energy level. In order to calculate the output spectrum at the X-ray detection circuit 15, we have to combine a plurality of response functions with respect to the actual emitted X-ray spectrum because the actual emitted X-ray spectrum has a broader X-ray spectrum than the monochromatic X-ray's spectrum. FIG. 5 shows the ideal response function from the X-ray detection circuit 15 that does not have pile-up. When the pile-up phenomena does occur, the response function shown in FIG. 5 should be corrected in consideration of the pile-up phenomena. The pile-up phenomena distorts the measured energy spectrum and results in a broader spectrum than the original distribution, and a shifted spectrum to higher energies than the original spectrum.

The main reasons for the above-described distortion are the pile-up phenomena and the characteristics of the X-ray detection circuit 15. This distortion is represented by formula (1).

$$Sin \otimes Resp = Sout \quad (1)$$

In formula (1), "Sin" represents the actual energy spectrum, and "Resp" represents the response function between the actual energy spectrum and the measured energy spectrum, and "Sout" represents the measured energy spectrum.

That is, the measured energy spectrum can be shown as a convolution with the response function "Resp" and the actual energy spectrum "Sin". According to this embodiment, the counting circuit 153 calculates the changed (corrected) count data emulating the actual energy spectrum by use of the response function and the measured energy spectrum. When the distortion detection circuit 33 detects the distortion on the measured energy spectrum "Sout" by checking the count data in the correction bin, the response function determining circuit 37 determines the response function "Resp" based on the number of counts in the correction bin. The count data correcting circuit 39 applies "Resp" to "Sout" to get collected count data emulating the actual energy spectrum "Sin". Note that the response function determining circuit 37 can determine the response function "Resp" based on a ratio between the number of counts at the target bin and the correction bin.

Note that a plurality of correction bins can be set at an energy range that exceeds the maximum energy level. For example, FIG. 4 shows two collection bins "binS1" and "binS2". A border between "binS1" and "binS2" can be set at the center energy level between Va [keV] and 2*Va [keV], but a location of the border can be varied based on a voltage value of the high-voltage signal from the high voltage generator 133 or an X-ray absorption filter attached to the X-ray tube 131.

According to this embodiment, the counting circuit 153 sets not only the target bins, but also the correction bin or bins. An energy range of the target bins and the correction bins can be modified by the input signal from the input circuit 47.

Figure 6:
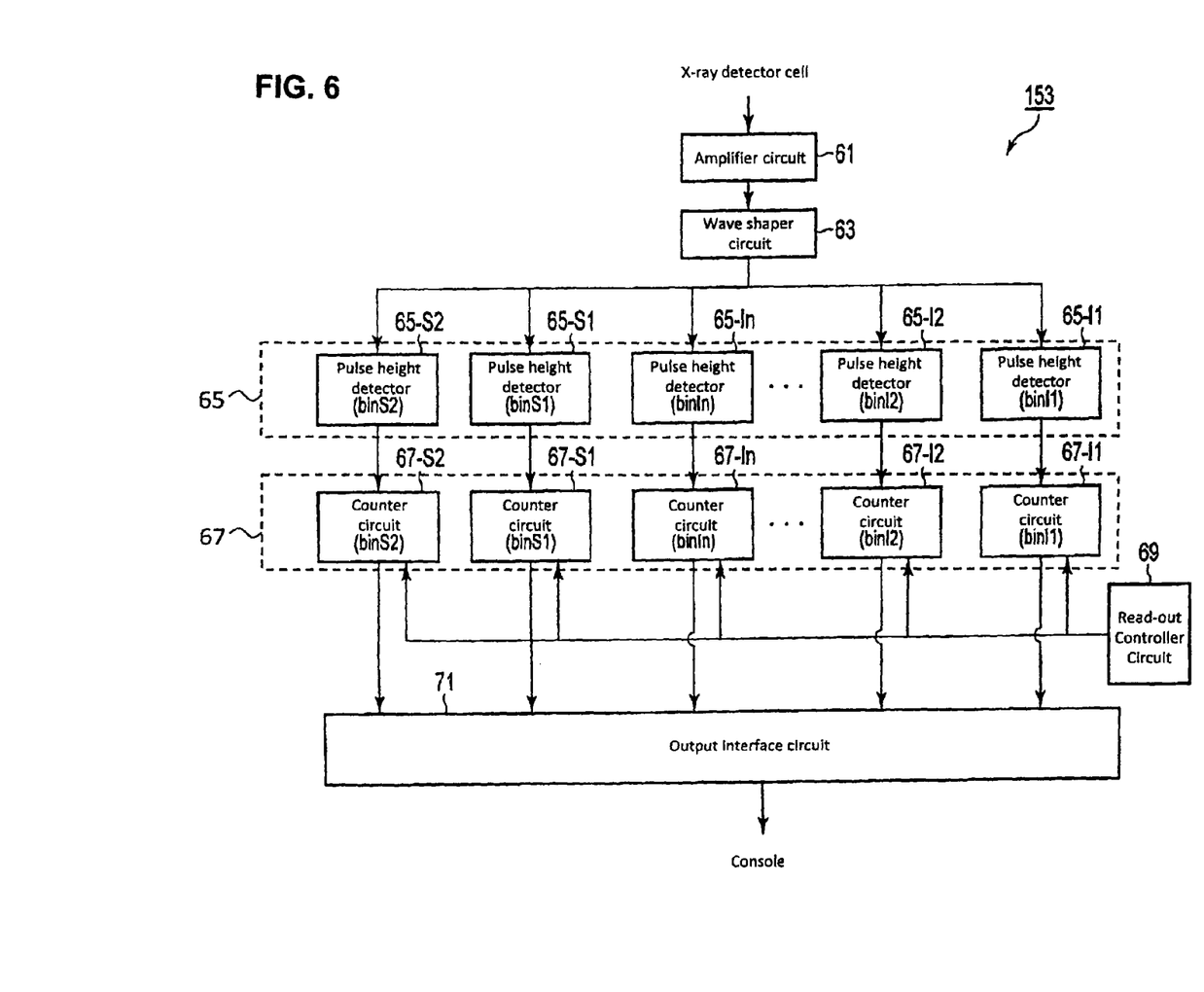
FIG. 6 is a block diagram of a counting circuit.

A composition of the counting circuit 153 will now be described. FIG. 6 shows an example of the counting circuit 153. The counting circuit 153 is comprised of processing circuitry such as integrated processors like a CPU, a FPGA, and/or a microprocessor. The counting circuit 153 has read-out channels, and the number of the read-out channels is the same as the number of X-ray detector cells. These read-out channels can be implemented as an electronic circuit ASIC (Application Specific Integrated Circuits). FIG. 6 shows one of the read-out channels as an example.

As shown in FIG. 6, the counting circuit 153 has circuit components including an amplifier circuit 61, a wave shaper circuit 63, a pulse height detector 65, a counter circuit 67, a read-out controller circuit 69, and an output interface circuit 71. For example, these circuit components can be implemented as an ASIC.

When an X-ray detector cell outputs the electronic pulse as a result of the incoming X-ray photon, the amplifier circuit 61 amplifies the electronic pulse and outputs the result to the wave shaper circuit 63. The wave shaper circuit 63 is connected to the amplifier circuit 61, reshapes the electronic pulse from the amplifier circuit 61, and outputs the result to the plurality of pulse height detector circuits 65. For example, the wave shaper circuit 63 has a low-pass filter, and the wave shaper circuit 63 removes high frequency noises from the electronic pulse by applying the low-pass filter. The wave shaper circuit 63 is connected to a plurality of pulse height detector circuits 65, and the number of the plurality of pulse height detector circuits 65 corresponds to the total number of the target bins and the correction bins. Thus, when the X (X is a integer above 1) energy bins are set to the energy spectrum, the number of pulse height detector circuits 65 is the same as X. In detail, FIG. 6 shows the n target bins and the two correction bins set to the energy spectrum. The pulse height detector circuit 65-I1 corresponds to the target bin "binI1", the pulse height detector circuit 65-I2 corresponds to the target bin "binI2", and the pulse height detector circuit 65-In corresponds to the target bin "binIn" in a same manner. The pulse height detector circuit 65-S1 corresponds to the target bin "binS1" and the pulse height detector circuit 65-S2 corresponds to the target bin "binS2".

Each of the pulse height detector circuits 65 has a different threshold and discriminates the energy of the X-ray photon using the threshold. In detail, when the pulse height detector circuit 65-X receives an electronic pulse with an energy level corresponding to the energy range X, the pulse height detector circuit 65-X outputs a detection signal. For example, when the pulse height detector circuit 65-S1 receives an electronic pulse with an energy level corresponding to the energy range S1, the pulse height detector circuit 65-S1 outputs the detection signal. The pulse height detector circuit 65 outputs this detection signal to the counter circuit 67.

The counter circuit 67, which includes counter circuits 67-S2, 67-S1, and 67-I1 to 67-In, as shown in FIG. 6, is connected to the pulse height detector circuit 65, and counts the detection signal from the pulse height detector circuit 65. The timing of this counting is controlled by a read-out signal from the read-out controller circuit 69. The read-out controller circuit 69 inputs the read-out signal to the output interface circuit 71 periodically. This cycle of reading-out is the same as a cycle of view change of the CT scan. The counter circuit 67 counts up the detection signal from the pulse height detector circuit 65 during this cycle. In detail, when the counter circuit 67 receives one detection signal, the counter circuit 67 increments a count number by 1. When the counter circuit 67 receives the read-out signal from the read-out controller circuit 69, the counter circuit 67 outputs the count number to the output interface circuit 71, and then resets the count number to 0.

The output interface circuit 71 is connected to the counter circuit 67 and outputs the count number to the count data memory 31 in the console 30 as the count data. The output interface circuit 71 outputs the count data with respect to each of the energy bins, the views, and the X-ray detector cells. That is, the output interface circuit 71 outputs count data corresponding to the number of energy bins and the number of channels and segments (rows) of the X-ray detector cells, for each of the views.

Above is a description of the counting circuit 153. As a result, the counting circuit 153 outputs count data for each of the target bins and the correction bins.

Note that the components of the counting circuit 153 can be arranged in different ways. For example, the pulse height detector 65 can be a multi-level pulse height detector that can discriminate the energy level using one circuit, instead of implementing the multiple pulse-height detectors 65 shown in FIG. 6.

An operation of the response function determining circuit 37 will now be described. As described above, the response function determining circuit 37 chooses a suitable response function based on the counts in the correction bins "binS". The chosen response function is applied to the count data for achieving the collected count data that emulates the actual energy spectrum. The response function determining circuit 37 chooses a suitable response function by referencing the count-response table stored by the response function memory 35. The count-response table is set using the recognition that a ratio between count numbers in "binS1" and "binS2" depends on a material composition that the X-rays traverse.

In detail, the count-response table is defined by a combination of two tables, a data-table showing a relationship between the output counts and the compositions of target tissue (a count-material table), and a data table showing a relationship between the compositions of target tissue and the response function (a material-response table). The count-material table is a look-up-table (LUT) that outputs a specific composition of the target tissue when receiving the specific output count. The material-response table is a LUT that outputs a specific response function when receiving the specific composition of the target tissue. Note that the count-response table as the combination of the count-material table and the material-response table is defined with respect to each of the parameters, including the high-voltage signal and the filament currents. The response function determining circuit 37 chooses the specific count-response table based on scanning parameters, including the high-voltage signal and the filament currents. The count-response table can be defined with respect to each of the scanning parameters, including the high-voltage signal, the filament current, and other parameters, like room temperature and an age of the X-ray detection circuit 15.

Figure 7:
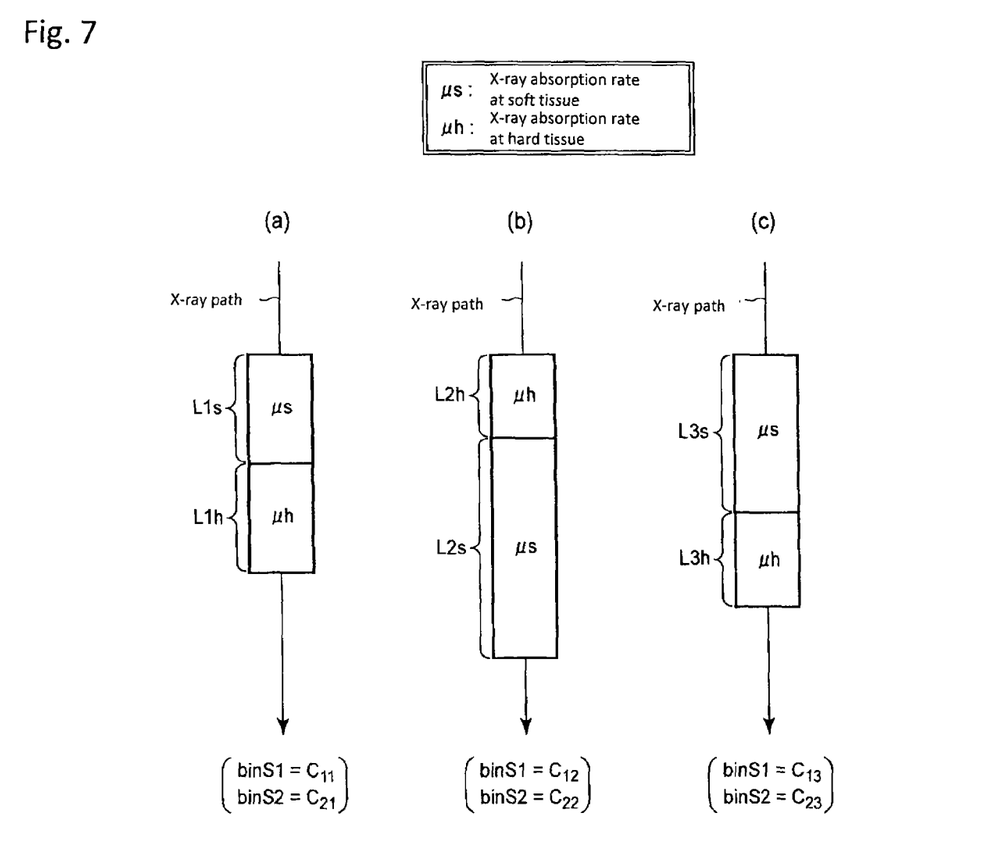
FIG. 7 shows dependency of output counts and a composition of a target tissue.

FIG. 7 shows an X-ray path that goes through the subject S. The composition of the target tissue is defined by a combination of a type of reference material and a material length. FIG. 7 shows an example of the target tissue that contains a soft tissue and a hard tissue. A leading example of the soft tissue is water and fat tissue. A leading example of hard tissue is bone. Now, we define an X-ray absorption rate of the soft tissues as "$\mu s$", and the X-ray absorption rate of the hard tissues as "$\mu h$". FIG. 7(a) shows the soft tissues with length "L1$s$" and the hard tissues with length "L1$h$" on the X-ray path. The counting circuit 153 shows the number of counts C11 in the correction bin "binS1" and the number of counts C21 in the correction bin "binS2" as an example. FIG. 7(b) shows the soft tissues with length "L2$s$" and the hard tissues with length "L2$h$" on the X-ray path. The counting circuit 153 shows the number of counts C12 in the correction bin "binS1" and the number of counts C22 in the correction bin "binS2" as a second example. FIG. 7(c) shows the soft tissues with length "L3$s$" and the hard tissues with length "L3$h$" on the X-ray path. The counting circuit 153 shows the number of counts C13 in the correction bin "binS1" and the number of counts C23 in the correction bin "binS2" as a third example.

As shown in FIGS. 7(a)-(c), the number of counts in the correction bins "binS1" and "binS2" depend on the length of the soft tissues and the hard tissues. This relationship can be estimated by experiments. Once this relationship is determined, when we know the combination of the number of counts in "binS1" and "binS2", we can estimate the composition of tissue lengths from this combination. Further, when we know the combination of the composition of tissues, we can estimate the appropriate response function that corrects the measured energy spectrum into the corrected energy spectrum emulating the actual energy spectrum.

An example of the count-material table and the material-response table stored by the response function memory 35 will now be described.

Figure 8:
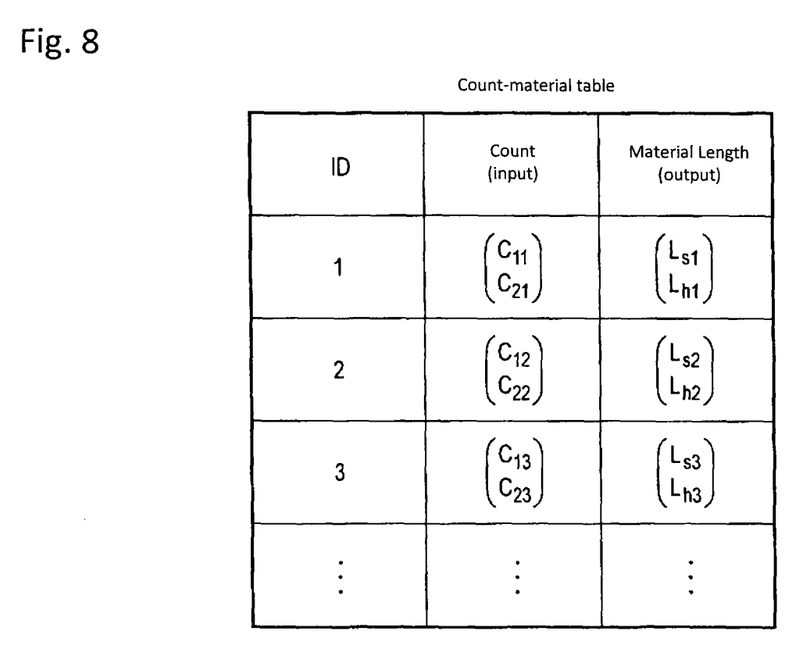
FIG. 8 is an example of a data table showing a relationship between the output counts and the composition of the target tissue.

FIG. 8 shows an example of a count-material table. Each of the count-material tables has a unique ID for ease of identification. The count-material table has two count data at "binS1" and "binS2" for each detector cell. For example, "C1$m$" in FIG. 8 represents the count number in "binS1", and "C2$m$" represents the count number in "binS2" of the count-material table that has ID "m". The count-material table has two length data for length of the soft tissue and the hard tissue, for each detector cell. "Lsm" represents the length of the soft tissue, and "Chm" represents the length of the hard tissue of the count-material table that has ID "m". These relationships can be determined by experiments using a phantom by a statistical simulation emulating the X-ray absorption. These data can be modified by an operator's input operation at the input circuit 47.

Figure 9:
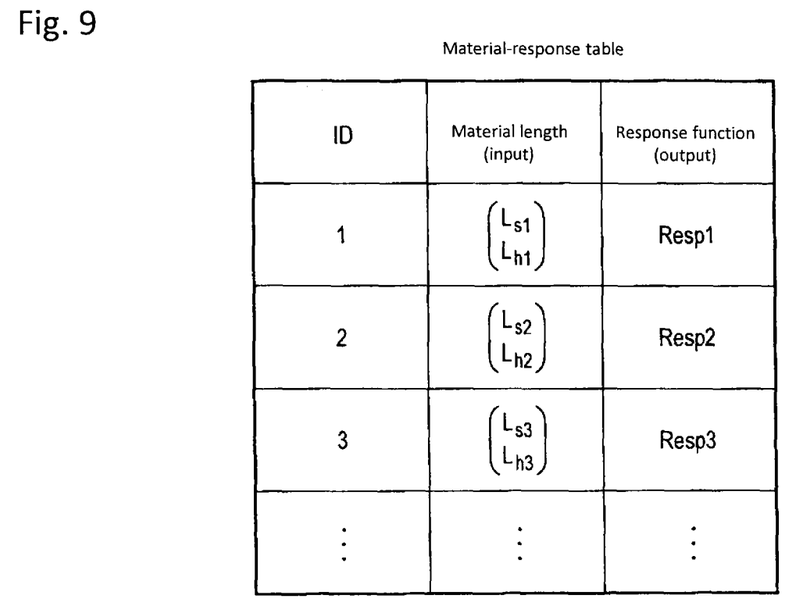
FIG. 9 is an example of a data table showing a relationship between a composition of the target tissue and a corresponding response function.

FIG. 9 shows an example of the material-response table. Similar to the count-material table, each of the material-response tables has a unique ID. The material-response table has two length data, similar to the count-material table. The material-response table has response functions corresponding to the combinations of the length data. The response functions represents a relationship between the measured energy spectrum and the actual energy spectrum described in formula 1. These relationships can be determined by experiments using a phantom by a statistical simulation emulating X-ray absorption. These data can be modified by an operator's input operation at the input circuit 47.

An operation of the response function determining circuit 37 will now be described.

Figure 10:
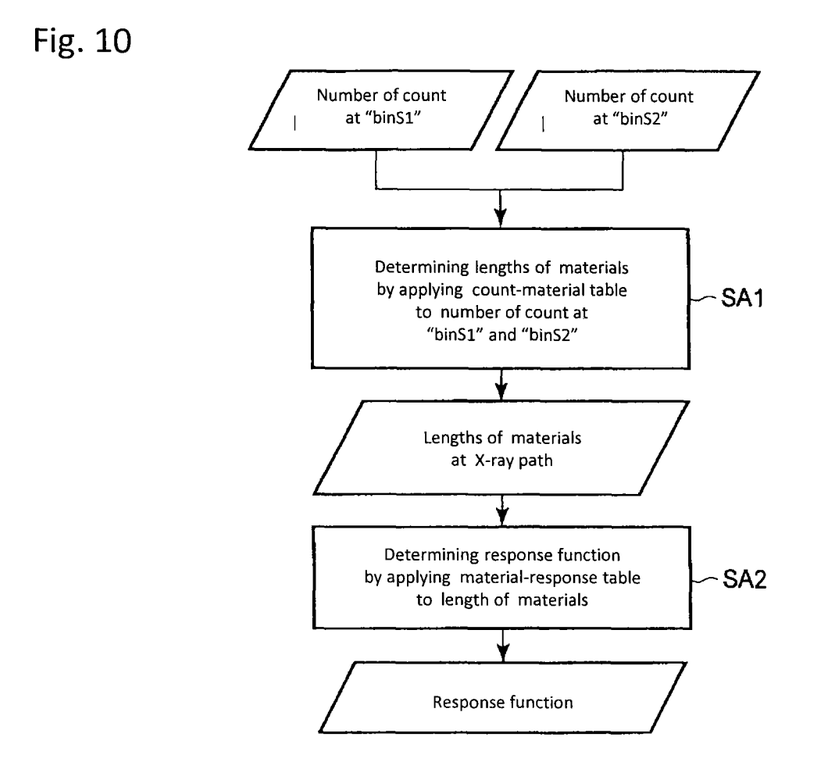
FIG. 10 is a flowchart showing a process for determining the response function according to one embodiment.

FIG. 10 shows a flowchart showing the steps that the response function determining circuit 37 executes, e.g., using a CPU programmed with program instructions, to determine the response function. This operation is executed with respect to each of the X-ray paths (each of the X-ray detector cells). As a first step, the response function determining circuit 37 reads out the count numbers at "binS1" and "binS2" from the count data memory 31 with respect to each of the X-ray paths.

Next, the response function determining circuit 37 determines the material length of the X-ray path, based on the count-material table and the count numbers at "binS1" and "binS2" (step SA1). For example, when the response function determining circuit 37 receives "C12" at "binS1" and "C22" at "binS2", the response function determine circuit 37 determines the combination of the material length that is "Ls2" for the soft tissue and "Lh2" for the hard tissue. Note that the pile-up phenomena causes the distortion that the count at "binI" shifts to the count at "binS". That is when the distortion occurs, the number of counts at "binI" is decreased and the number of counts at "binS" is increased. In order to correct this shift, the response function can be defined to compensate for the increased count number at "binS". In this case, the response function will be defined so as to meet two boundaries. The first boundary is that the count numbers in "binS1" and "binS2" will equal the count number estimated by the material length "Ls2" for the soft tissue and "Lh2" for the hard tissue. The second boundary is that the total count number in "binS1" and "binS2" will be added to the count number in "binI".

As a next step, the response function determining circuit 37 determines the response function for the X-ray path based on the material-response table and the material length at step SA1 (step SA2). For example, when the material length "Ls3" for the soft tissue and "Lh3" for the hard tissue is inputted to the material-response table, the response function determining circuit 37 determines "Resp3" as the response function.

By repeating these steps for each of the X-ray paths, the response function determining circuit 37 determines the response function for each of the X-ray paths. In a similar manner, by repeating these steps, the response function determining circuit 37 determines the response function for each of the X-ray paths that are needed for image reconstruction by the reconstruction circuit 41.

Note that the steps that determine the response function for correcting the distortion can be omitted when the X-ray paths do not have the pile-up phenomena. When the X-ray paths do not have the pile-up phenomena, the response function determining circuit 37 outputs a default response function instead of the response function that is determined by the count-response table. The distortion detection circuit 33 can detect the pile-up phenomena by checking the count numbers in "binS1" and "binS2". When the distortion detection circuit 33 detects that the total count number in "binS1" and "binS2" is below a certain threshold value, the response function determining circuit 37 outputs the default response function instead of executing the steps shown in FIG. 10. These operations can speed up the whole process of reconstructing a photon-counting CT image.

Figure 11:
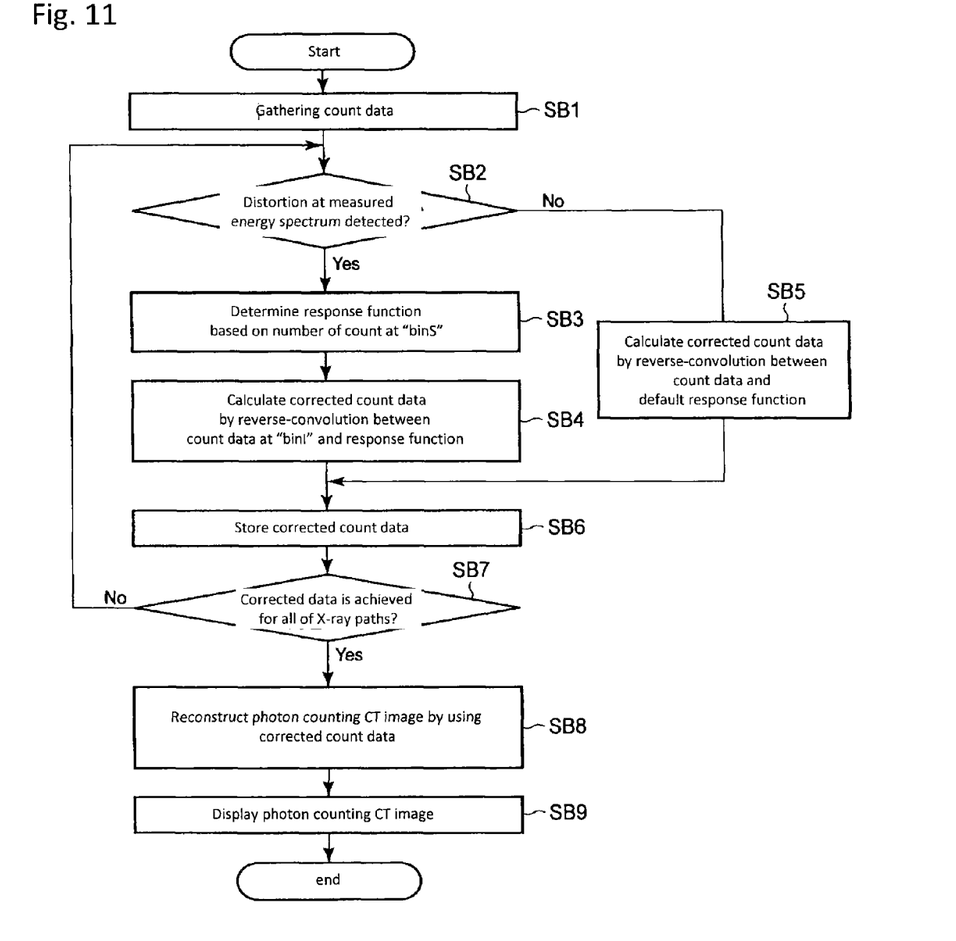
FIG. 11 is a flowchart showing a process for a photon-counting CT scan according to one embodiment.

FIG. 11 shows an entire flow of a CT scan procedure controlled by the system controller circuit 51. The steps in FIG. 11 can be executed, e.g., by a CPU (processing circuit) programmed with program instructions to implement the functions shown in FIG. 11 and described herein. For example, as noted above, each of elements 33, 37, 39, 41, 51, and 153 can be implemented by at least one CPU (processing circuit) that executes program instructions. For example, the counting circuit 153 executes step SB1 in FIG. 11, while distortion detection circuit 33 executes step SB2.

As a first step, when the input circuit 47 inputs a command for starting the CT scan to the system controller circuit 51, the system controller circuit 51 causes the rotating frame 11 to rotate and the X-ray generator circuit 13 to start emitting X-rays toward the subject S. The X-ray detection circuit 15 gathers the count data and outputs the count data to the count data memory 31 (step SB1). In detail, the system controller circuit 51 sends the command for starting the CT scan to the gantry 10 via the I/F circuit 43. When the gantry control circuit 21 receives this command, the gantry control circuit 21 controls the X-ray generator circuit 13, the X-ray detection circuit 15, and the rotation control circuit 19 for emitting the X-rays to the subject S. The counting circuit 153 outputs the count data in "binI" and "binS" to the count data memory 31.

Figure 3:
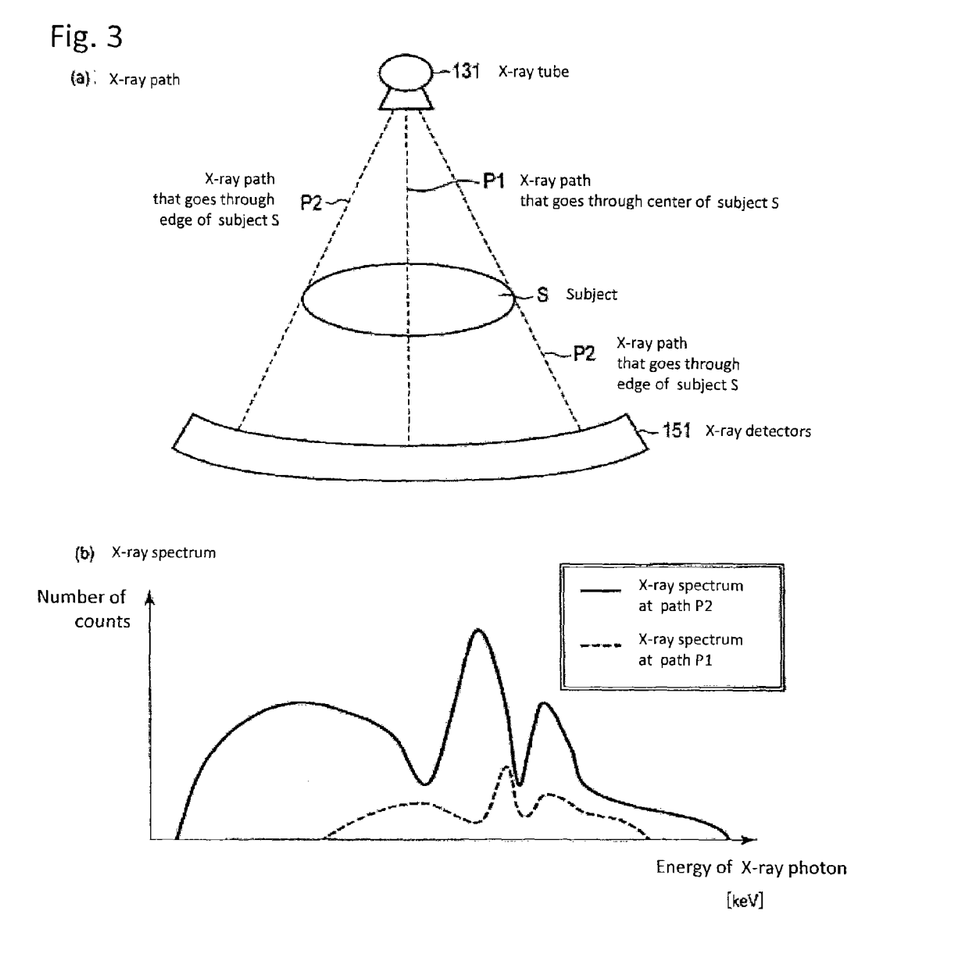
FIG. 3 shows the dependency of an X-ray path and the incoming energy spectrum.

When step SB1 is finished, the system controller circuit 51 causes the distortion detection circuit 33 to detect any distortion based on the count data in "binS" (step SB2). In detail, the distortion detection circuit 33 checks the number of counts in "binS". When the number of counts in "binS" exceeds a predetermined threshold, the distortion detection circuit 33 detects the distortion that distorts the measured energy spectrum from the actual energy spectrum. This comparison between the number of counts in "binS" and the predetermined threshold is executed with respect to each of the X-ray paths (or the X-ray detector cells) for each view. As described above, when the pile-up phenomena occurs, the measured energy spectrum will be distributed over the maximum energy corresponding to the correction bin "binS". The maximum energy depends on the voltage value of the high-voltage signal applied to the X-ray tube 131 by the high-voltage generator 133. For example, as shown in FIG. 3, the possibility that the pile-up phenomena has occurred to the X-ray path that passes through the center of the subject S is low, and the possibility that the pile-up phenomena has occurred to the X-ray path that goes through the edge of the subject S is relatively high.

As described above, the correction bins "binS1" and "binS2" are set by the counting circuit 153. The distortion detection circuit 33 can compare the predetermined threshold with a statistical value of "binS1" and "binS2", such as an average count of "binS1" and "binS2", a maximum count of "binS1" and "binS2", a minimum count of "binS1" and "binS2", a total count of "binS1" and "binS2", and a median count of three or more correction bins. Alternatively, the distortion detection circuit 33 can compare the predetermined threshold and either of "binS1" and "binS2". The predetermined threshold can be determined by experiments using a phantom or by a statistical simulation emulating the X-ray absorption. This threshold can be modified by an operator's input operation at the input circuit 47.

When the distortion detection circuit 33 detects the distortion (step SB2: Yes), the system controller circuit 51 causes the response function determining circuit 37 to determine the response function (step SB3). At step SB3, the response function determining circuit 37 determines the response function by using the count data in "binS1" and "binS2", the count-response table, and the scanning parameters, like the high-voltage signal, the filament current, and other parameters, such as room temperature and an age of the X-ray detection circuit 15. The response function determining circuit 37 determines the response function for each of the X-ray paths for each view.

After step SB3, the system controller circuit 51 causes the count data correcting circuit 37 to apply the response function to the count data to generate corrected count data (step SB4). At step SB4, the count data correcting circuit 37 executes reverse convolution on the count data using the response function determined by the response function determining circuit 37. The count data correcting circuit 37 calculates the corrected count data by the reverse convolution.

When the distortion detection circuit 33 does not detect the distortion (step SB2: No), the system controller circuit 51 causes the count data correcting circuit 37 to execute reverse-convolution on the count data using the default response function determined by the response function determining circuit 37 (step SB5). As described above, the default response function is applied when the distortion does not occur to the measured energy spectrum. For a simpler explanation, the count data that is applied to the default response function is also the collected count data, the same as in step SB4.

When the step SB4 or the step SB5 is finished, the system controller circuit 51 causes the count data memory 31 to store the corrected count data. The count data memory 31 stores the changed (corrected) count data in associate with an ID number of the X-ray path.

When the step SB6 is finished, the system controller circuit 51 checks that the procedure for generating the corrected count data is finished for the all of the X-ray paths (step SB7). When there are X-ray paths for which the count data correcting circuit 39 has not generated corrected count data yet (step SB7: No), the system controller circuit 51 goes back to step SB2. The system controller circuit 51 repeats steps SB2 to SB7 until all of the corrected count data is generated.

When all of the changed (corrected) count data is generated (step SB7: Yes), the system controller circuit 51 causes the reconstruction circuit 41 to reconstruct the photon-counting CT image using the changed (corrected) count data (step SB8). At step SB8, the reconstruction circuit 41 reads out the corrected count data for "binI" for all of the X-ray paths used for the reconstruction. The reconstruction circuit 41 generates sinogram data by sorting the corrected count data along with the ID number of the X-ray path (ray number). Then the reconstruction circuit 41 reconstructs the photon-counting CT image at the target bins, by applying the reconstruction algorithm to the corrected count data. For example, the reconstruction circuit 41 can use FBP (Filtered Back Projection) and CBP (Convolution Back Projection) as analytical reconstruction algorithms, or ML-EM (Maximum Likelihood Expectation Maximization) and OS-EM (Ordered Subset Expectation Maximization) as statistical reconstruction algorithms.

After step SB9, the system controller circuit 51 finishes the CT scan procedure according to this embodiment.

Note that the distortion detection operation by the distortion detection circuit 33 can omit certain X-ray paths. For example, the distortion detection circuit 33 can skip the distortion detection operation for the X-ray path that passes through the center of the subject S, and execute the distortion detection operation as described in step SB2 for the X-ray path that passes through the edge of the subject S. In this case, the omitted X-ray path will be applied in step SB5. This modification can omit step SB3 and step SB4 for the X-ray paths that have a low possibility of having distortion, and speeds up the entire process.

In another embodiment, three or more types of reference material can be set in the material-response table.

As described above, the X-ray generator circuit 13 emits X-rays to the subject S. The X-ray detection circuit 15 detects the X-ray photons, and the counting circuit 153 outputs the count data to the console 30. The count data represents the number of counts of the X-ray photons coming into the X-ray detector cells. The response function determining circuit 37 determines the response function for correcting the measured energy spectrum. The response function determining circuit 37 determines the response function based on the number of counts that have an energy level exceeding the maximum energy of the emitted X-ray spectrum. The count data correcting circuit 39 generates the corrected data by applying the response function to the count data.

In this embodiment, the photon-counting CT can correct the measured energy spectrum by using the response function. That is, the photon-counting CT can generate corrected count data so that the effects of the pile-up phenomena and the difference of detection characteristics of the X-ray detector cells are cancelled. Then the photon-counting CT can reconstruct the photon-counting CT image with a high image quality.

In one embodiment, the photon-counting CT can correct the distortion at the measured energy spectrum with high accuracy.

Note that in one embodiment, the photon-counting CT has a $3^{rd}$-generation structure. That is, the rotating frame 11 of the photon-counting CT rotates both the X-ray generator circuit 13 and the X-ray detection circuit 15, as a rotate/rotate-type CT. However, a structure of the photon-counting CT can be arranged as a $4^{th}$-generation structure or other structures. When the photon-counting CT has the $4^{th}$-generation structure, the X-ray detector cells are fixed around the gantry 10, and the rotating frame 11 rotates the X-ray generator circuit 13 as a stationary/rotate-type CT.

Note that the present inventions are not limited to the above embodiments, and constituent elements can be variously modified and embodied at the execution stage within the spirit and scope of the inventions. In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined. And the components described above can be implemented as several separated hardware circuits as shown in FIG. 1, and also can be integrated in a single hardware circuit.

The invention claimed is:

1. A photon-counting type X-ray computed tomography apparatus, comprising:
   a high-voltage generator configured to generate a voltage signal;
   an X-ray tube configured to emit X-rays when the X-ray tube receives the voltage signal from the high-voltage generator;
   an X-ray detector configured to detect photons derived from the X-rays emitted from the X-ray tube; and
   circuitry configured to
      detect a first number of photons within a first energy band that exceeds an energy level corresponding to a voltage value of the voltage signal, wherein the first energy band includes a third energy band and a fourth energy band,
      detect a second number of photons within a second energy band that is below the energy level corresponding to the voltage value of the voltage signal, wherein the second energy band includes a fifth energy band and a sixth energy band, and change the second number of photons within the second energy band, based on the detected first number of photons within the first energy band, to correct for operational limitations of the X-ray detector, wherein the circuitry is further configured to correct a number of photons in the fifth and sixth energy bands based on a number of photons in the third and fourth energy bands.

2. The photon-counting type X-ray computed tomography apparatus according to claim 1, further comprising:
a memory circuit configured to store a plurality of response functions, wherein the circuitry is further configured to
choose one of the response functions stored in the memory circuit based on the detected first number of the photons at the first energy band, and
change the second number of the photons at the second energy band by applying the chosen response function to the second number of the photons at the second energy band.

3. The photon-counting type X-ray computed tomography apparatus according to claim 1, wherein
the circuitry is further configured to reconstruct a photon-counting CT image based on the changed second number of the photons at the second energy band.

4. The photon-counting type X-ray computed tomography apparatus according to claim 2, wherein
the memory circuit stores an association data table associating the plurality of the response functions with the first number of the photons at the first energy band, and
the circuitry is further configured to choose one of the response functions stored in the memory circuit based on the first number of the photons at the first energy band using the association data table.

5. The photon-counting type X-ray computed tomography apparatus according to claim 4, wherein the association data table comprises
a first data table associating the first number of the photons at the first energy band with a material length of path of the X-rays,
a second data table associating the material length with a corresponding response function of the response functions.

6. The photon-counting type X-ray computed tomography apparatus according to claim 2, wherein
the circuitry is further configured to choose the one of the response functions based on a combination of the number of the photons in the third energy band and the fourth energy band.

7. The photon-counting type X-ray computed tomography apparatus according to claim 2, wherein the circuitry is further configured to choose a response function with respect to each of paths of the X-rays.

8. The photon-counting type X-ray computed tomography apparatus according to claim 2, wherein
the circuitry is further configured to change the second number of the photons at the second energy band by reverse-convoluting the number of the second photons at the second energy band with the chosen response function.

9. The photon-counting type X-ray computed tomography apparatus according to claim 1, wherein
the circuitry is further configured to
determine if a pile-up phenomena occurs at a path of the X-rays, and
change the number of the photons at the second energy band at the path for which the pile-up phenomena has occurred.

10. The photon-counting type X-ray computed tomography apparatus according to claim 9, wherein
the circuitry is further configured to reconstruct a photon-counting CT image based on the changed number of the photons for the path for which the pile-up phenomena has occurred, and a number of the photons for a path for which the pile-up phenomena has not occurred.

11. The photon-counting type X-ray computed tomography apparatus according to claim 3, further comprising:
a display that displays the photon-counting CT image reconstructed by the circuitry.

12. A method for correcting photon-counting data obtained by a photon-counting type X-ray computed tomography apparatus, comprising:
counting a number of photons resulting from X-rays emitted from an X-ray tube;
detecting a first number of the photons within a first energy band that exceeds an energy level corresponding to a voltage value of a voltage signal that is applied to the X-ray tube for emitting the X-rays, wherein the first energy band includes a third energy band and a fourth energy band;
detecting a second number of photons within a second energy band that is below the energy level corresponding to the voltage value of the voltage signal, wherein the second energy band includes a fifth energy band and a sixth energy band,
changing the second number of the photons within the second energy band, based on the first number of the photons detected within the first energy band, to correct for operational limitations of the X-ray detector,
wherein the changing step comprises correcting a number of photons in the fifth and sixth energy bands based on a number of photons in the third and fourth energy bands.

* * * * *